United States Patent [19]
Giesen et al.

[11] Patent Number: 5,658,875
[45] Date of Patent: Aug. 19, 1997

[54] ULTRAMILD SURFACTANT MIXTURES

[75] Inventors: Brigitte Giesen; Wolfgang Pittermann, both of Duesseldorf; Karl Schmid, Mettmann; Walter Sterzel, Duesseldorf, all of Germany

[73] Assignee: Henkel Kommanditgesellschaft auf Aktien, Duesseldorf, Germany

[21] Appl. No.: 557,151

[22] PCT Filed: Jun. 7, 1994

[86] PCT No.: PCT/EP94/01844

§ 371 Date: Dec. 14, 1995

§ 102(e) Date: Dec. 14, 1995

[87] PCT Pub. No.: WO94/29417

PCT Pub. Date: Dec. 22, 1994

[30] Foreign Application Priority Data

Jun. 16, 1993 [DE] Germany .................. 43 19 699.3

[51] Int. Cl.$^6$ ........................................ C11D 3/22
[52] U.S. Cl. ........................................ 510/470
[58] Field of Search ................ 510/470, 130, 510/151, 218, 219, 234, 356, 135

[56] References Cited

U.S. PATENT DOCUMENTS

| | | | |
|---|---|---|---|
| 3,721,633 | 3/1973 | Ranauto ................ | 510/405 |
| 4,483,779 | 11/1984 | Llenado et al. .......... | 510/324 |
| 4,668,422 | 5/1987 | Malik et al. ............ | 510/135 |
| 4,673,525 | 6/1987 | Small et al. ............ | 510/151 |
| 4,820,447 | 4/1989 | Medcalf, Jr. et al. ..... | 510/151 |
| 5,035,814 | 7/1991 | Maaser ................ | 8/137 |
| 5,258,142 | 11/1993 | Giesen et al. .......... | 510/537 |
| 5,264,144 | 11/1993 | Moroney et al. ......... | 510/151 |
| 5,286,406 | 2/1994 | Scholz et al. ........... | 510/158 |
| 5,370,816 | 12/1994 | Balzer et al. ........... | 510/340 |
| 5,374,716 | 12/1994 | Biermann et al. ........ | 536/18.6 |
| 5,389,282 | 2/1995 | Saijo et al. ............. | 510/416 |
| 5,395,543 | 3/1995 | Johansson et al. ....... | 510/229 |

FOREIGN PATENT DOCUMENTS

| | | |
|---|---|---|
| 0301298 | 2/1989 | European Pat. Off. . |
| 0384983 | 9/1990 | European Pat. Off. . |
| 0444262 | 9/1991 | European Pat. Off. . |
| 4005958 | 8/1991 | Germany . |
| WO903977 | 4/1990 | WIPO . |
| WO93/23512 | 11/1993 | WIPO . |

OTHER PUBLICATIONS

Skin Care Forum, 1, (Oct. 1992).
Seifen –Oele –Fette –Wachse 118, 894 (1992).
Seifen –Oele –Fette –Wachse 118, 905 (1992).
J. Falbe (ed.), "Surfactants in Consumer Products", Springer Verlag, Berlin 1987, pp. 54–124.
J. Falbe (ed.), "Katalystoren, Tenside und Mineraloeladditive", Thieme Verlag, Stuttgart, 1978, pp. 123–217.
"Kosmetische Faerbemittel" of the Farbstoffkommission der Detschen Forschungsgeminschaft, published by Verlag Chemie, Weinheim, 1984.

Primary Examiner—Paul Lieberman
Assistant Examiner—John R. Hardee
Attorney, Agent, or Firm—Wayne C. Jaeschke; John E. Drach; Henry E. Millson, Jr.

[57] ABSTRACT

An ultramild surfactant mixture consisting of a) from about 5 to about 12% by weight of at least one alkyl oligoglucoside corresponding to formula (I):

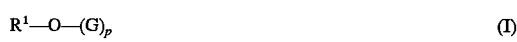

$$R^1\text{—O—}(G)_p \qquad (I)$$

in which $R^1$ is an alkyl radical containing 8 to 10 carbon atoms, G is a glucose unit and p is a number of 1.3 to 1.8; and b) from about 88 to about 95% by weight of at least one alkyl oligoglucoside corresponding to formula (II):

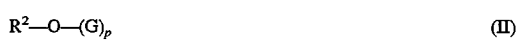

$$R^2\text{—O—}(G)_p \qquad (II)$$

in which $R^2$ is an alkyl radical containing 12 to 16 carbon atoms, G is a glucose unit and p is a number of 1.3 to 1.8. Also, finished compositions containing the above surfactant mixture.

4 Claims, 1 Drawing Sheet

ULTRAMILD SURFACTANT MIXTURES

BACKGROUND OF THE INVENTION

1. Field of the Invention

This invention relates to surfactant mixtures with improved dermatological compatibility which contain alkyl oligoglucosides having a selected chain length composition.

2. Statement of Related Art

Alkyl oligoglycosides, especially alkyl oligoglucosides, are nonionic surfactants which are acquiring increasing significance by virtue of their excellent detergent properties and their high ecotoxicological compatibility. The production and use of these substances have been described just recently in a number of synoptic articles of which the articles by H. Hensen in Skin Care Forum, 1, (October 1992), D. Balzer and N. Ripke in Seifen-Öle-Fette-Wachse 118, 894 (1992) and B. Brancq in Seifen-Öle-Fette-Wachse 118, 905 (1992) are cited as representative.

Although alkyl oligoglucosides are extremely mild on the skin, there is still a growing need for substances having further improved dermatological compatibility. For example, attempts have been made in the past to improve the dermatological compatibility of alkyl oligoglucosides by addition of amphoteric surfactants.

A starting point for the production of particularly high-performance alkyl oligoglucosides is to mix species differing in their chain length. For example, it is proposed in hitherto unpublished patent application U.S. Ser. No. 07/876,967 (Henkel Corp.) to mix two alkyl oligoglucosides having chain lengths of $C_{8-10}$ and $C_{12-16}$ in a ratio of 50:50 to 90:10 parts by weight. However, this application teaches using a mixing ratio of 60:40 to 80:20, i.e. using the short-chain species in excess.

DE-A1 40 05 958 (Hüls) describes a liquid foaming cleaning preparation which may contain 3 to 40% by weight of a $C_{7-10}$ alkyl oligoglucoside and 3 to 40% by weight of a $C_{11-18}$ alkyl oligoglucoside (ad 100% by weight water). It is proposed to use the relatively short-chain and relatively long-chain species in a ratio by weight of 10:90 to 50:50 and preferably in a ratio of 17:83 to 33:67. There is no reference in this document to particular advantages arising out of the dermatological compatibility of the mixture.

In the past, alkyl oligoglucosides differing in their chain length have been mixed primarily with a view to obtaining optimal performance properties. Although the mixtures according to the prior art may be satisfactory, for example, in regard to their foaming and cleaning power, their dermatological compatibility is not optimal.

Now, the problem addressed by the present invention was to provide new mixtures of alkyl oligoglucosides differing in their chain lengths which would be free from the disadvantages mentioned above.

DESCRIPTION OF THE INVENTION

The present invention relates to ultramild surfactant mixtures containing a) 5 to 12% by weight of an alkyl oligoglucoside corresponding to formula (I):

$$R^1\text{—O—}(G)_p \qquad (I)$$

in which $R^1$ is a $C_{6-12}$ alkyl radical, G is a glucose unit and p is a number of 1.3 to 1.8 and b) 88 to 95% by weight of an alkyl oligoglucoside corresponding to formula (II):

$$R^2\text{—O—}(G)_p \qquad (II)$$

in which $R^2$ is a $C_{10-18}$ alkyl radical, G is a glucose unit and p is a number of 1.3 to 1.8.

It has surprisingly been found that products showing particularly high dermatological compatibility can be obtained within a very narrow mixing range of alkyl oligoglucosides differing in their chain length. Although similar mixtures of short-chain and long-chain alkyl oligoglucosides in a ratio of 10:90 are mentioned as lower limits in DE-A1 40 05 958 (Hüls), the selection made in accordance with the present application is both new and inventive because neither the mixtures as such nor the surprising effect associated with them have been described before and because the teaching of the cited document points in the direction of mixing ratios at which the advantageous dermatological compatibility is no longer present.

Alkyl oligoglucosides

Alkyl oligoglucosides are known substances which may be obtained by the relevant methods of preparative organic chemistry. EP-A1-0 301 298 and WO 90/3977 are cited as representative of the extensive literature available on this subject.

The index p in general formulae (I) and (II) indicates the degree of oligomerization (DP degree), i.e. the distribution of monoglucosides and oligoglucosides and is a number of 1.3 to 1.8. Whereas p in a given compound must always be an integer and, above all, may assume a value of 1.3 to 1.6, the value p for a certain alkyl oligoglucoside is an analytically determined calculated quantity which is generally a broken number.

The alkyl radical $R^1$ may be derived from primary alcohols containing 6 to 12 and preferably 8 to 10 carbon atoms. Typical examples are caproic alcohol, caprylic alcohol, 2-ethylhexyl alcohol, capric alcohol, undecyl alcohol and lauryl alcohol and technical mixtures thereof such as are obtained, for example, in the hydrogenation of technical fatty acid methyl esters or in the hydrogenation of aldehydes from Roelen's oxosynthesis. $C_{6-12}$ alkyl oligoglucosides (DP=1.3 to 1.6), which are obtained as first runnings in the separation of technical $C_{8-18}$ coconut oil fatty alcohol by distillation and which contain essentially $C_{8-10}$ alkyl radicals, are preferred. Alkyl oligoglucosides corresponding to formula (I) which have the following C chain distribution in the alkyl radical are particularly preferred:

$C_6$:0–5% by weight
$C_8$:40–66% by weight
$C_{10}$:30–59% by weight
$C_{12}$:0–6% by weight The alkyl radical $R^2$ may be derived from primary alcohols containing 10 to 18 and preferably 12 to 16 carbon atoms. Typical examples are capric alcohol, lauryl alcohol, myristyl alcohol, cetyl alcohol, stearyl alcohol, isostearyl alcohol, arachyl alcohol, behenyl alcohol and technical mixtures thereof which may be obtained as described above. Alkyl oligoglucosides based on hydrogenated $C_{10-18}$ coconut oil alcohol (DP=1.3 to 1.6), in which the alkyl radicals essentially contain 12 to 16 carbon atoms, are preferred. Alkyl oligoglucosides corresponding to formula (II) which have the following C chain distribution in the alkyl radical are particularly preferred:

$C_{10}$:0–3% by weight
$C_{12}$:60–75% by weight
$C_{14}$:21–30% by weight
$C_{16}$:0–12% by weight
$C_{18}$:0–3% by weight Production of the mixtures The alkyl oligoglucosides corresponding to formulae (I) and (II) may be mixed by methods known per se. For example, the concentrated pastes may be stirred with one another at an elevated temperature of 40° C. and may be diluted to the in-use concentration during making up into end products. However, dilute solutions may also be mixed with one another in the same way. This entails a purely mechanical operation involving no chemical reaction.

In one preferred embodiment of the invention, however, the relatively short-chain alkyl oligoglucosides may also be added to the relatively long-chain alkyl oligoglucosides during their production, for example before the final bleaching step. In addition, it is possible—taking the differences in reactivity into account—to acetalize fatty alcohols of suitable chain composition with glucose by methods known per se and thus to produce the mixtures in situ. In both these cases, uniform products are obtained.

COMMERCIAL APPLICATIONS

Figure 1:
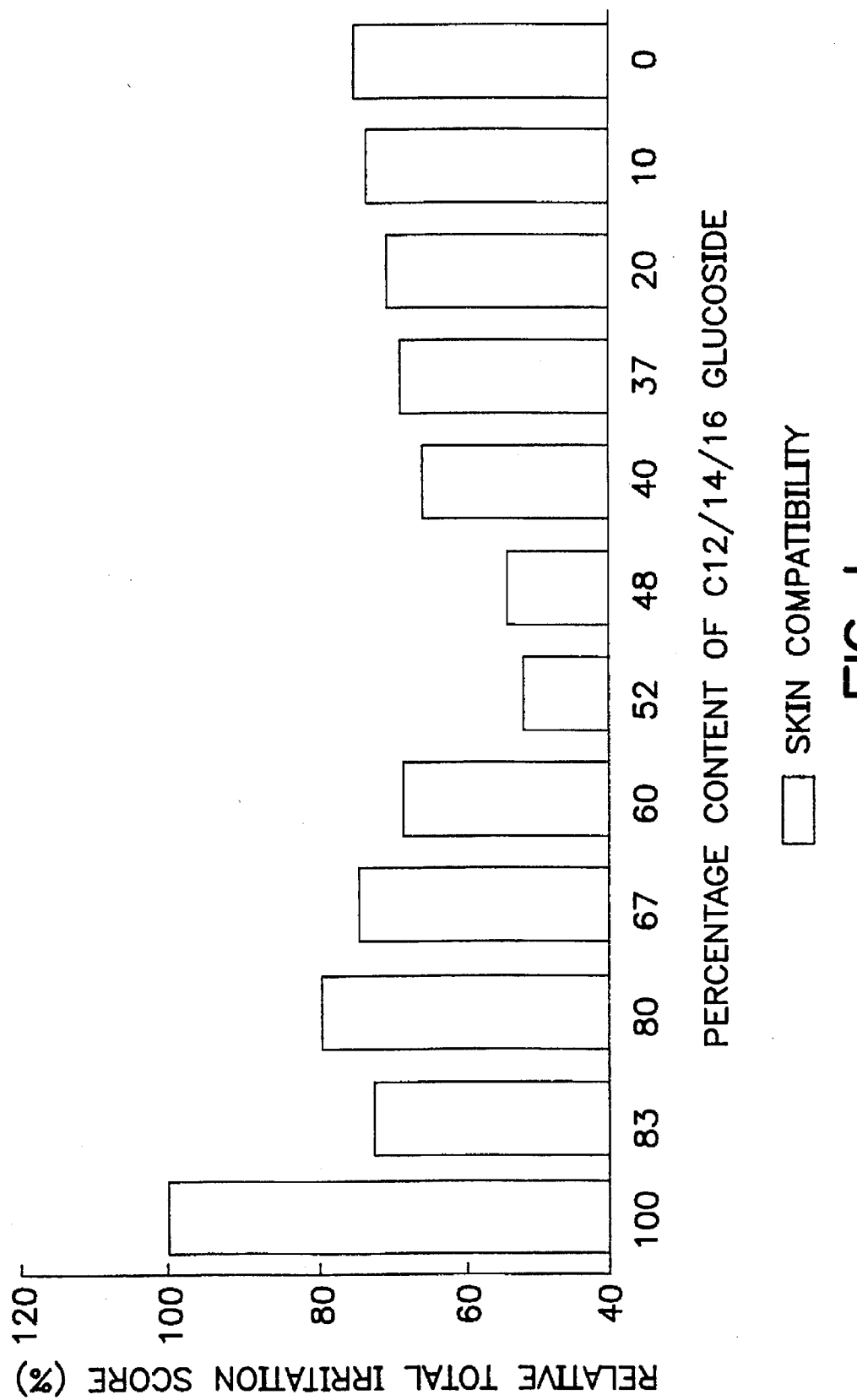
FIG. 1 plots total irritation scores for mixtures of alkyl oligoglycosides. The data are summarized in Table 1.

The surfactant mixtures according to the invention are distinguished by particularly high dermatological compatibility and do not irritate the skin, even in the form of 50% by weight aqueous pastes.

Surfactants

The surfactant mixtures according to the invention may be used together with other anionic, nonionic, cationic and/or amphoteric or zwitterionic surfactants.

Typical examples of anionic surfactants are alkyl benzenesulfonates, alkanesulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, monoglyceride sulfates, fatty acid amide (ether) sulfates, sulfosuccinates, sulfosuccinamates, sulfotriglycerides, amide soaps, ether carboxylic acids, fatty acid isethionates, sarcosinates, taurides, alkyl oligoglucoside sulfates, alkyl (ether) phosphates and vegetable or animal protein hydrolyzates or condensation products thereof with fatty acids. Where the anionic surfactants contain polyglycol ether chains, they may have a conventional homolog distribution although they preferably have a narrow homolog distribution.

Typical examples of nonionic surfactants are fatty alcohol polyglycol ethers, alkyl phenol polyglycol ethers, fatty acid polyglycol esters, fatty acid amide polyglycol ethers, fatty amine polyglycol ethers, alkoxylated triglycerides, alk(en)yl oligoglycosides, fatty acid glucamides, polyol fatty acid esters, sugar esters, sorbitan esters and polysorbates. Where the nonionic surfactants contain polyglycol ether chains, they may have a conventional homolog distribution although they preferably have a narrow homolog distribution.

Typical examples of cationic surfactants are quaternary ammonium compounds and quaternized difatty acid trialkanolamine esters.

Typical examples of amphoteric or zwitterionic surfactants are alkyl betaines, alkyl amidobetaines, aminopropionates, aminoglycinates, imidazolinium betaines and sulfobetaines.

All the surfactants mentioned are known compounds. Information on the structure and production of these substances can be found in relevant synoptic works, cf. for example J. Falbe (ed.), "Surfactants in Consumer Products", Springer Verlag, Berlin 1987, pp. 54–124 or J. Falbe (ed.), "Katalysatoren, Tenside und Mineralöladditive", Thieme Verlag, Stuttgart, 1978, pp. 123–217.

Surface-active preparations

The present invention also relates to the use of the surfactant mixtures according to the invention for the production of surface-active preparations, more particularly laundry detergents, dishwashing detergents and cleaning products and also hair-care and personal-care products, in which they may be present in quantities of 1 to 99% by weight and preferably in quantities of 5 to 30% by weight, based on the particular preparation. The following are typical examples of such preparations:

Powder-form universal detergents containing 10 to 30% by weight—based on the detergent—of the mixture according to the invention of alkyl oligoglucosides corresponding to formulae (I) and (II) and anionic, nonionic, cationic and/or amphoteric or zwitterionic surfactants and, optionally, other typical auxiliaries and additives.

Liquid universal detergents containing 10 to 70% by weight—based on the detergent—of the mixture according to the invention of alkyl oligoglucosides corresponding to formulae (I) and (II) and anionic, nonionic, cationic and/or amphoteric or zwitterionic surfactants and, optionally, other typical auxiliaries and additives.

Liquid light-duty detergents containing 10 to 50% by weight—based on the detergent—of the mixture according to the invention of alkyl oligoglucosides corresponding to formulae (I) and (II) and anionic, nonionic, cationic and/or amphoteric or zwitterionic surfactants and, optionally, other typical auxiliaries and additives.

Liquid cleaning and disinfecting preparations containing 10 to 30% by weight—based on the preparation—of the mixture according to the invention of alkyl oligoglucosides corresponding to formulae (I) and (II) and anionic, nonionic, cationic and/or amphoteric or zwitterionic surfactants and, optionally, other typical auxiliaries and additives.

Hair shampoos containing 10 to 30% by weight—based on the shampoo—of the mixture according to the invention of alkyl oligoglucosides corresponding to formulae (I) and (II) and anionic, nonionic, cationic and/or amphoteric or zwitterionic surfactants and, optionally, other typical auxiliaries and additives.

Hair rinses containing 10 to 30% by weight—based on the hair rinse—of the mixture according to the invention of alkyl oligoglucosides corresponding to formulae (I) and (II) and anionic, nonionic, cationic and/or amphoteric or zwitterionic surfactants and, optionally, other typical auxiliaries and additives.

Foam baths containing 10 to 30% by weight—based on the foam bath—of the mixture according to the invention of alkyl oligoglucosides corresponding to formulae (I) and (II) and anionic, nonionic, cationic and/or amphoteric or zwitterionic surfactants and, optionally, other typical auxiliaries and additives.

Syndet soaps containing 10 to 50% by weight—based on the soap—of the mixture according to the invention of alkyl oligoglucosides corresponding to formulae (I) and (II) and anionic, nonionic, cationic and/or amphoteric or zwitterionic surfactants and, optionally, other typical auxiliaries and additives.

Detergents and cleaning products based on the detergent mixtures according to the invention may contain, for example, builders, salts, bleaches, bleach activators, optical brighteners, redeposition inhibitors, solubilizers, foam inhibitors and enzymes as auxiliaries and additives.

Typical builders are sodium aluminium silicates (zeolites), phosphates, phosphonates, ethylenediamine tetraacetic acid, nitrilotriacetate, citric acid and/or polycarboxylates. Suitable salts or diluents are, for example, sodium sulfate, sodium carbonate or sodium silicate (waterglass). Typical individual examples of other additives are sodium borate, starch, sucrose, polydextrose, TAED, stilbene compounds, methyl cellulose, toluene sulfonate, cumene sulfonate, long-chain soaps, silicones, mixed ethers, lipases and proteases.

Hair shampoos, hair lotions or foam baths based on the detergent mixtures according to the invention may contain, for example, emulsifiers, oil components, fats and waxes, thickeners, superfatting agents, biogenic agents, film formers, fragrances, dyes, pearlescers, preservatives and pH regulators as auxiliaries and additives.

Typical oil components are such substances as paraffin oil, vegetable oils, fatty acid esters, squalene and 2-octyl dodecanol. Suitable fats and waxes are, for example, spermaceti, beeswax, montan wax, paraffin and cetostearyl alcohol. Superfatting agents may be selected from such substances as, for example, polyethoxylated lanolin derivatives, lecithin derivatives and fatty acid alkanolamides, the fatty acid alkanolamides also serving as foam stabilizers. Suitable thickeners are, for example, polysaccharides, more particularly xanthan gum, guar guar, agar agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone and electrolytes, such as sodium chloride and ammonium chloride. Biogenic agents are understood to be, for example, vegetable extracts, protein hydrolyzates and vitamin complexes. Typical film formers are, for example, polyvinyl pyrrolidone, vinyl pyrrolidone/vinyl acetate copolymers, polymers of the acrylic acid series, quaternary cellulose derivatives and similar compounds. Suitable preservatives are, for example, formaldehyde solution, p-hydroxybenzoate or sorbic acid. Suitable pearlescers are, for example, glycol distearic acid esters, such as ethylene glycol distearate, and also fatty acid monoglycol esters. The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984. These dyes are typically used in concentrations of 0.001 to 0.1% by weight, based on the mixture as a whole.

The following Examples are intended to illustrate the invention without limiting it in any way

EXAMPLES

I. Alkyl oligoglucosides used
Comp. I:
$C_{8-10}$ alkyl oligoglucoside
C chain distribution in the alkyl radical: 45% $C_8$, 55% $C_{10}$
DP degree: 1.59
Plantaren® APG 225, a product of Henkel KGaA, Düsseldorf, FRG
Comp. II:
$C_{12-16}$ coconut oil alkyl oligoglucoside
C chain distribution in the alkyl radical: 68% $C_{12}$, 26% $C_{14}$, 6% $C_{16}$
DP degree: 1.38–1.53
Plantaren® APG 600, a product of Henkel KGaA, Düsseldorf, FRG All the products were used in the form of 50% by weight aqueous pastes.

II. Application Examples

Irritation of the skin was determined by OECD Method No. 404 and EEC Directive 84/449 EEC, Part B.4. The total irritation scores shown were compiled from the irritation scores obtained after 24, 48 and 72 hours. The total irritation score determined in comparison test C1 for a 100% $C_{12-16}$ alkyl oligoglucoside (DP=1.38) was put at 100% and the total irritation scores obtained in the other tests were related to that score.

The results are set out in Table 1 and FIG. 1.

TABLE 1

Results of performance tests

| Ex. | Comp. I % by weight | Comp. II % by weight | DP | Total irritation score % rel. |
|---|---|---|---|---|
| 1 | 7 | 93 | 1.38 | 67 |
| 2 | 10 | 90 | 1.38 | 62 |
| 3 | 10 | 90 | 1.41 | 60 |
| 4 | 10 | 90 | 1.53 | 52 |
| 5 | 12 | 88 | 1.38 | 59 |
| C1 | 0 | 100 | 1.38 | 100 |
| C2 | 0 | 100 | 1.45 | 95 |
| C3 | 0 | 100 | 1.53 | 95 |
| C4 | 17 | 83 | 1.38 | 72 |
| C5 | 20 | 80 | 1.38 | 80 |
| C6 | 33 | 67 | 1.38 | 75 |
| C7 | 40 | 60 | 1.38 | 64 |
| C8 | 60 | 40 | 1.38 | 62 |
| C9 | 63 | 37 | 1.38 | 70 |
| C10 | 80 | 20 | 1.38 | 72 |
| C11 | 90 | 10 | 1.38 | 75 |
| C12 | 100 | 0 | 1.38 | 78 |
| C12 | 100 | 0 | 1.59 | 71 |

We claim:

1. An ultramild surfactant mixture consisting of:

a) from about 5 to about 12% by weight of at least one alkyl oligoglucoside corresponding to formula (I):

$$R^1\text{—O—}(G)_p \qquad (I)$$

in which $R^1$ is an alkyl radical containing 8 to 10 carbon atoms, G is a glucose unit and p is a number of 1.3 to 1.8; and b) from about 88 to about 95% by weight of at least one alkyl oligoglucoside corresponding to formula (II:

$$R^2\text{—O—}(G)_p \qquad (II)$$

in which $R^2$ is an alkyl radical containing 12 to 16 carbon atoms, G is a glucose unit and p is a number of 1.3 to 1.8.

2. The surfactant mixture of claim 1 wherein component a) is a mixture of alkyl oligoglucosides in which $R^1$ represents alkyl radicals having the following C chain distribution: $C_6$: 0–5% by weight, $C_8$: 40–66% by weight, $C_{10}$: 30–59% by weight, and $C_{12}$: 0–6% by weight.

3. The surfactant mixture of claim 1 wherein component b) is a mixture of alkyl oligoglucosides in which $R^2$ represents alkyl radicals having the following C chain distribution: $C_{10}$: 0–3% by weight, $C_{12}$: 60–75% by weight, $C_{14}$:

21–30% by weight, $C_{16}$: 0–12% by weight, and $C_{18}$: 0–3% by weight.

4. The surfactant mixture of claim 2 wherein component b) is a mixture of alkyl oligoglucosides in which $R^2$ represents alkyl radicals having the following C chain distribution: $C_{10}$: 0–3% by weight, $C_{12}$: 60–75% by weight, $C_{14}$: 21–30% by weight, $C_{16}$: 0–12% by weight, and $C_{18}$: 0–3% by weight.

* * * * *